US010702444B2

(12) United States Patent
Idowu et al.

(10) Patent No.: US 10,702,444 B2
(45) Date of Patent: *Jul. 7, 2020

(54) NON-SURGICAL TORSO DEFORMITY CORRECTION DEVICES AND METHODS RELATED THERETO

(71) Applicant: Children's Hospital & Research Center at Oakland, Oakland, CA (US)

(72) Inventors: Olajire Idowu, Lafayette, CA (US); Sunghoon Kim, San Ramon, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 297 days.

This patent is subject to a terminal disclaimer.

(21) Appl. No.: 15/821,565

(22) Filed: Nov. 22, 2017

(65) Prior Publication Data

US 2018/0153761 A1 Jun. 7, 2018

Related U.S. Application Data

(63) Continuation of application No. 14/266,447, filed on Apr. 30, 2014, now Pat. No. 9,855,184.

(60) Provisional application No. 61/821,609, filed on May 9, 2013.

(51) Int. Cl.
*A61H 9/00* (2006.01)
*A61B 17/02* (2006.01)

(52) U.S. Cl.
CPC ........ *A61H 9/0057* (2013.01); *A61B 17/0281* (2013.01); *A61H 2201/1619* (2013.01); *A61H 2201/5064* (2013.01); *A61H 2201/5071* (2013.01); *A61H 2205/084* (2013.01)

(58) Field of Classification Search
CPC ................. A61H 7/00; A61H 9/0057; A61H 2201/1619; A61H 2201/5064; A61H 2205/084; A61M 27/00; A61B 17/0281
See application file for complete search history.

(56) References Cited

U.S. PATENT DOCUMENTS

| 87,370 A | 3/1869 | Schnebly |
| 197,142 A | 11/1877 | Jones |
| 603,004 A | 4/1898 | Booth |
| 655,747 A | 8/1900 | Winckfield |

(Continued)

*Primary Examiner* — Justine R Yu
*Assistant Examiner* — Christopher E Miller
(74) *Attorney, Agent, or Firm* — Shweta Chandra; Bozicevic, Field & Francis LLP

(57) ABSTRACT

Aspects of the invention include devices and methods for correcting a torso deformity of a patient. The devices include a suction chamber for placement around the torso deformity and to provide negative pressure to the torso deformity; and a measurement component coupled to the suction chamber. The measurement component is adapted to indicate a relative distance between the torso deformity and a distal surface of the suction chamber. The methods include positioning a torso deformity correcting device around a torso deformity on a torso of a patient. The methods further include withdrawing air from the suction chamber to apply negative pressure within the suction chamber to displace the torso deformity, and setting a negative pressure level by measuring the relative distance of the torso deformity and the distal surface of the suction chamber that is indicated by the measurement component.

19 Claims, 4 Drawing Sheets

(56) References Cited

U.S. PATENT DOCUMENTS

| | | | |
|---|---|---|---|
| 2,529,258 A | 11/1950 | Gonzalez | |
| 3,032,034 A | 5/1962 | Martin | |
| 3,078,842 A | 2/1963 | Gray | |
| 4,444,191 A | 4/1984 | Harned | |
| 4,469,105 A | 9/1984 | Staver | |
| 4,483,075 A | 11/1984 | Kundin | |
| 4,523,579 A * | 6/1985 | Barry | A61H 31/02 601/44 |
| 4,635,618 A | 1/1987 | Munz | |
| 5,007,895 A | 4/1991 | Burnett | |
| 5,076,259 A * | 12/1991 | Hayek | A61H 31/02 601/44 |
| 5,295,481 A | 3/1994 | Geeham | |
| 5,573,498 A * | 11/1996 | Hayek | A61H 31/02 601/41 |
| 5,807,280 A | 9/1998 | Davis | |
| 5,820,572 A | 10/1998 | Palmer | |
| D401,326 S | 11/1998 | Powell | |
| 5,865,722 A | 2/1999 | Heng | |
| 6,042,539 A | 3/2000 | Harper | |
| 6,098,205 A | 8/2000 | Schwartz et al. | |
| 6,146,362 A | 11/2000 | Turnbull et al. | |
| 6,159,167 A | 12/2000 | Hardin | |
| 6,254,614 B1 | 7/2001 | Jesseph | |
| 6,322,484 B1 | 11/2001 | Muller | |
| 6,345,618 B1 * | 2/2002 | Hayek | A61H 31/02 128/202.12 |
| 6,394,977 B1 | 5/2002 | Taylor | |
| 6,409,638 B1 | 6/2002 | Huston | |
| 6,475,124 B1 | 11/2002 | Weiss | |
| 6,485,467 B1 | 11/2002 | Crook | |
| 6,540,707 B1 | 4/2003 | Stark et al. | |
| 6,951,546 B2 | 10/2005 | Palmer et al. | |
| 7,229,422 B2 | 6/2007 | Klobe | |
| 7,401,413 B1 | 7/2008 | Nelson | |
| 9,855,184 B2 | 1/2018 | Idowu et al. | |
| 2002/0022796 A1 | 2/2002 | Lawrence | |
| 2003/0220594 A1 | 11/2003 | Halvorson et al. | |
| 2004/0073150 A1 | 4/2004 | Roballey | |
| 2004/0243073 A1 | 12/2004 | Lockwood | |
| 2005/0119700 A1 | 6/2005 | Klobe | |
| 2006/0178601 A1 | 8/2006 | Wang et al. | |
| 2007/0066946 A1 | 3/2007 | Haggstrom et al. | |
| 2008/0058851 A1 | 3/2008 | Edelstein | |
| 2009/0054929 A1 | 2/2009 | Pajares Mellado | |
| 2010/0137874 A1 | 6/2010 | Kim et al. | |
| 2010/0168630 A1 | 7/2010 | Cropper et al. | |
| 2011/0028898 A1 | 2/2011 | Clark, III et al. | |
| 2011/0172576 A1 | 7/2011 | Castro | |
| 2011/0230806 A1 | 9/2011 | Lou et al. | |
| 2012/0116276 A1 | 5/2012 | Marinez Ferro et al. | |
| 2012/0209161 A1 | 8/2012 | Castro | |
| 2012/0302923 A1 | 11/2012 | Santiago | |
| 2013/0035611 A1 | 2/2013 | White | |
| 2013/0041303 A1 | 2/2013 | Hopman et al. | |
| 2013/0197315 A1 | 8/2013 | Foley | |
| 2013/0281272 A1 | 10/2013 | Payne | |

\* cited by examiner

NON-SURGICAL TORSO DEFORMITY CORRECTION DEVICES AND METHODS RELATED THERETO

CROSS REFERENCE TO RELATED APPLICATIONS

Under 35 U.S.C. § 119(e), this application claims priority to the filing date of U.S. Provisional Patent Application Ser. No. 61/821,609, filed on May 9, 2013, the disclosure of which application is herein incorporated by reference in its entirety.

BACKGROUND

Pectus excavatum is a deformity of the anterior wall of the chest that results in a depression or hollow in the chest. For instance, the ribs and sternum may grow abnormally and result in a caved-in or sunken appearance of the chest. Pectus excavatum is sometimes referred to as funnel chest, sunken chest, or cobbler's chest. Pectus excavatum may be congenital or may develop within months of birth. Torso deformities, such as pectus excavatum, may be treated with surgery in moderate to severe cases, or alternatively may be treated by applying suction pressure to the torso deformity. Too little pressure applied to the torso deformity may result in ineffective or slow treatment. Too much pressure applied to the torso deformity may cause skin irritation, pain, and/or discomfort to the patient.

SUMMARY

Aspects of the invention include devices and methods for correcting a torso deformity of a patient. The devices include a suction chamber for placement around the torso deformity and to provide negative pressure to the torso deformity; and a measurement component coupled to the suction chamber. The measurement component is adapted to indicate a relative distance between the torso deformity and a distal surface of the suction chamber. The methods include positioning a torso deformity correcting device around a torso deformity on a torso of a patient. The methods further include withdrawing air from the suction chamber to apply negative pressure within the suction chamber to displace the torso deformity, and setting a negative pressure level by measuring the relative distance of the torso deformity and the distal surface of the suction chamber that is indicated by the measurement component.

Aspects of the invention include a device for correcting a torso deformity of a patient, the device including a suction chamber for placement around the torso deformity and to provide negative pressure to the torso deformity, and a measurement component coupled to the suction chamber, wherein the measurement component is adapted to indicate a relative distance between the torso deformity and a distal surface of the suction chamber. In some embodiments, the measurement component represents a distance that the torso deformity is displaced by the negative pressure. In some embodiments, the measurement component includes an elongated member moveably coupled to the suction chamber for visual measurement of the distance between the distal surface of the suction chamber and the torso deformity. In some embodiments, the elongated member is moveably coupled to the suction chamber through an air-tight port. In some embodiments, the air-tight port includes an elongated septum extending into the suction chamber, and the elongated member is disposed within the air-tight port and the elongated septum. In some embodiments, the air-tight port is located in a central portion of the suction chamber. In some embodiments, the elongated member includes a plurality of indicator marks. In some embodiments, the elongated member is removable.

In some embodiments, the device further includes a pressure gauge that provides a visual verification of the negative pressure level inside the suction chamber. In some embodiments, the pressure gauge includes an elastic material that is displaced as a function of the amount of negative pressure applied to the suction chamber.

In some embodiments, the device further includes a retaining element coupled to the suction chamber to maintain the suction chamber in place when positioned around the torso deformity. In some embodiments, the device further includes a suction pump operably coupled to the suction chamber for withdrawal of air contained between the suction chamber and the torso when the suction chamber is positioned around the torso deformity.

Aspects of the invention include a method of correcting a torso deformity of a patient, the method involving positioning a torso deformity correcting device around a torso deformity on a torso of a patient, wherein the device includes a suction chamber for placement around the torso deformity and to provide negative pressure to the torso deformity, and a measurement component coupled to the suction chamber, wherein the measurement component is adapted to indicate a relative distance between the torso deformity and a distal surface of the suction chamber, withdrawing air from the suction chamber to apply negative pressure within the suction chamber to displace the torso deformity, and setting a negative pressure level by measuring the relative distance of the torso deformity and the distal surface of the suction chamber that is indicated by the measurement component.

In some embodiments, the measurement component represents a distance that the torso deformity is displaced by the negative pressure. In some embodiments, the measurement component includes an elongated member moveably coupled to the suction chamber for visual measurement of the distance between the distal surface of the suction chamber and the torso deformity. In some embodiments, the elongated member is moveably coupled to the suction chamber through an air-tight port. In some embodiments, the air-tight port includes an elongated septum extending into the suction chamber, and the elongated member is disposed within the air-tight port and the elongated septum. In some embodiments, the air-tight port is located in a central portion of the suction chamber. In some embodiments, the elongated member comprises a plurality of indicator marks. In some embodiments, the elongated member is removably coupled to the suction chamber, and the method further involves removing the elongated member from the suction chamber after the negative pressure level is set.

In some embodiments, the device further includes a pressure gauge that provides a visual verification of the negative pressure level inside the suction chamber, and the method further involves visually verifying the negative pressure level set inside the suction chamber with the pressure gauge. In some embodiments, the elongated member is moveably coupled to the suction chamber through an air-tight port. In some embodiments, the method further involves removing the elongated member from the suction chamber after the negative pressure level is set, and the negative pressure level is visually verified after the elongated member is removed. In some embodiments, the pressure gauge comprises an elastic material that is displaced as a function of the amount of negative pressure applied to the suction chamber. In some embodiments, the device further includes a retaining element coupled to the suction chamber, and the method further involves retaining the suction chamber around the torso deformity with the retaining element after the suction chamber is positioned around the torso deformity. In some embodiments, the device further includes a suction pump operably coupled to the suction chamber, and the method further involves withdrawing air contained between the suction chamber and the torso with the suction pump when the suction chamber is positioned around the torso deformity.

DETAILED DESCRIPTION

Figure 1:
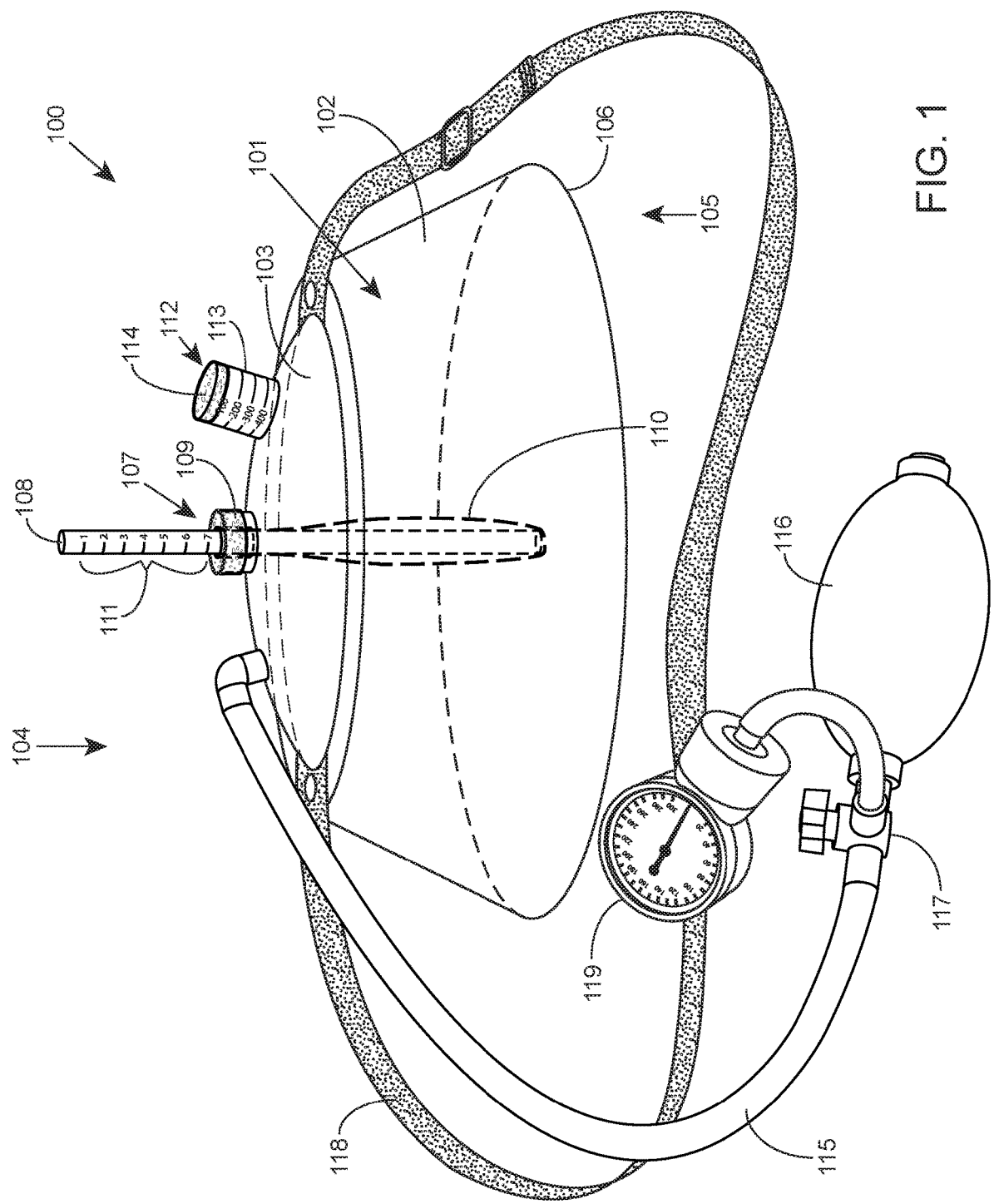
FIG. 1 illustrates a perspective view of the torso deformity correction device, according to certain embodiments.

Aspects of the invention include devices and methods for correcting a torso deformity of a patient. The devices include a suction chamber for placement around the torso deformity and to provide negative pressure to the torso deformity; and a measurement component coupled to the suction chamber. The measurement component is adapted to indicate a relative distance between the torso deformity and a distal surface of the suction chamber. The methods include positioning a torso deformity correcting device around a torso deformity on a torso of a patient. The methods further include withdrawing air from the suction chamber to apply negative pressure within the suction chamber to displace the torso deformity, and setting a negative pressure level by measuring the relative distance of the torso deformity and the distal surface of the suction chamber that is indicated by the measurement component.

In some aspects, the devices and methods disclosed herein relate to the correction of torso deformities where the patient's torso is deformed and sunken inwards, such as pectus excavatum. Suction may be applied to the anterior side of a torso deformity over time to correct the deformity in a non-surgical manner. The subject devices and methods are described in further detail below.

Devices

In some aspects, devices for correcting a torso deformity of a patient are provided. The devices include a suction chamber for placement around the torso deformity and to provide negative pressure to the torso deformity; and a measurement component coupled to the suction chamber. The measurement component is adapted to indicate a relative distance between the torso deformity and a distal surface of the suction chamber.

The torso deformity correction device includes a suction chamber for placement around the torso deformity. The suction chamber may include a distal side and an open proximal side such that when the device is positioned on the torso of the patient around the torso deformity, the suction chamber and the anterior side of the torso of the patient forms an inner cavity of air. When negative pressure is applied to the suction chamber, such as by a suction pump, the pressure inside the suction chamber is decreased. Decreasing the pressure within the suction chamber in relation to the higher pressure outside of the suction chamber creates a suction that is applied to the torso deformity. As more air is withdrawn from the suction chamber, the suction pressure that pulls on the torso deformity increases. The suction pump may include a manual pump, such as a suction bulb for example, or may include, e.g., an electric vacuum source to withdraw air from the suction chamber.

The suction chamber may be made from any variety of materials but should generally be sufficiently non-permeable to air to function as a suction device. Example materials may include, for example, metals, metal-alloys, polymeric materials such as hard or soft plastics, etc. Materials that are not completely rigid (e.g., softer polymeric materials that have some rigidity) may be used to provide better comfort for the user.

The suction chamber may vary in size in different embodiments. The size of the suction chamber may vary based on patient size, deformity size, suction pressure required, etc. For example, the diameter of the suction chamber may be within a range of 18 inches or less, such as 12 inches or less, including 8 inches or less. It should be appreciated that larger suction chamber sizes are also possible, and furthermore, that the suction chamber may be a shape other than circular, such as oval, square, triangular, or any other regular or irregular shape.

The measurement component provides an indication of the relative distance between the torso deformity and a distal surface of the suction chamber. The relative distance will change as negative pressure is applied to the suction chamber. In certain embodiments, the measurement component includes an elongated member that is disposed within an airtight port. The elongated member may be inserted within the port and extended to the torso deformity, and thus may serve as a distance measurement to the torso deformity. The elongated member is movably coupled within the port of the suction chamber such that when the torso deformity is displaced outwardly by suction pressure, the torso deformity pushes the elongated member in a direction out of the port. In this way, the portion of the elongated member that is extending outside of the port may be visually monitored by an operator to determine the relative distance between the torso deformity and the distal surface of the suction chamber (e.g., the distal surface where the port is located). In certain embodiments, the elongated member is removably coupled to the port so that the elongated member may be removed.

In certain embodiments the measurement component includes an elongated member that is disposed within an airtight port having an airtight septum. For example, in certain embodiments, the airtight port includes an elongated septum that extends into the suction chamber. The elongated member is disposed within the airtight port and the inner lumen formed by the elongated septum. The elongated member may move within the port without loss of air because it remains on the outside of the elongated septum, which prevents loss of air from inside the suction chamber. The elongated member is movable such that it may extend to the torso deformity when the device is positioned on the patient.

The septum may be made from any variety of materials but should enable an airtight seal to prevent air loss. In certain embodiments, instead of an elongated septum, the airtight septum may comprise an expandable ring. For example, the ring may be positioned in the port and around the elongated member. In some embodiments, the ring may be made from an expandable material such as a rubber or other polymeric material, and may be biased to sufficiently press against the elongated member to provide an airtight seal but still enable the elongated member to slide within the port. In certain embodiments where the elongated member is removable, the ring may be biased such that in a normal state the center of the ring is sufficiently closed to prevent air loss. In this way, when the elongated member is not present, the ring closes to provide an airtight seal. However, when the elongated member is inserted into the port, the elongated member penetrates the center of the ring and expands the ring. The ring is biased to sufficiently press against the elongated member to provide an airtight seal but still enable the elongated member to slide within the port.

In certain embodiments, the measurement component is disposed in the center of the suction chamber. In this way, the elongated member extends to the approximate center of the torso deformity that the suction chamber is positioned around. In other embodiments, the elongated member may not be centrally disposed in the suction chamber.

The elongated member may range in size but should be long enough to reach the surface of the torso deformity. Example size ranges may include, but are not limited to, about 10 inches or less, such as about 7 inches or less, including about 5 inches or less. When the elongated member extends to the surface of the torso deformity, as the torso deformity is displaced by the negative pressure, the torso deformity pushes the elongated member and displaces the elongated member through the port. In this way, the elongated member indicates the relative distance between the distal surface and the torso deformity. In certain embodiments, the elongated member includes indicator markings to facilitate determining the amount of displacement of the torso deformity.

It should be appreciated that the suction chamber may compress or otherwise shift closer to the torso upon application of negative pressure within the suction chamber—e.g., when the suction chamber is not completely rigid. Furthermore, in some embodiments, a rim of the suction chamber may include a compressible element that compresses when negative pressure is applied to the suction chamber. For example, the rim may include rubber, other semi-soft polymeric materials, and/or one or more chambers that can be filled with, e.g., air, water, gel, or other media, that compresses when negative pressure is applied thereto. In such cases, the suction chamber and/or the compressible element on the rim may compress upon application of negative pressure and change the relative distance between the torso deformity and a distal surface of the suction chamber. Thus, the relative distance will be affected by the displacement of the torso deformity from the suction pressure, as well as by the compression of the suction chamber and/or compressible element on the rim. It should be appreciated that in such case, the measuring component may still be used by the operator (e.g., a physician or caregiver) as a guide or approximation of the distance that the torso deformity has been displaced. For embodiments with a more rigid suction chamber that does not compress, the distance that the torso deformity is displaced by suction is more accurately mirrored by the distance that the elongated member is displaced out of the port.

In certain embodiments, the correction device optionally includes a pressure gauge that provides a visual verification of the negative pressure level inside the suction chamber. For example, a pressure gauge may be coupled to the suction chamber to provide a measurement reading of the pressure level within the suction chamber. In certain embodiments, the pressure gauge includes an opening and an elastic material disposed around the opening. As negative pressure is applied to the suction chamber, the elastic material is pulled within the opening to provide a visual indication of the level of negative pressure. Any variety of elastic materials may be used, such as but not limited to polymeric materials that provide an airtight seal. The degree of elasticity may be selected based on the degree of movement desired for the measurement reading. In some instances, the pressure gauge may include indicator markings to represent the negative pressure level associated with the amount of displacement of the elastic material. In certain embodiments, the elongated member of the measurement component is removable, and the pressure gauge provides visual verification of the negative pressure level inside the suction chamber after the elongated member has been removed.

In some embodiments, the correction device may optionally include a pressure gauge mounted on one or more components of the suction pump for visually verifying the amount of negative pressure applied to the suction chamber. For example, in some embodiments, a pressure gauge may be attached to the tubing that connects a suction bulb to the suction chamber, and the pressure gauge is used to visually verify the amount of negative pressure applied to the suction chamber with the suction bulb.

In certain embodiments, the correction device includes a retaining element that maintains the suction chamber in place when positioned around the torso deformity. This may assist the placement of the suction chamber around the torso deformity by holding it in place before sufficient negative pressure is applied to form a suction to the torso. In some embodiments, the retaining element is coupled to the sides of the suction chamber. The retaining element is positioned around the patient and may be adjusted in length to maintain the suction chamber in place before using the suction pump. The retaining element may be made from any variety of materials sufficient to hold the suction chamber in place. Example materials may include, but are not limited to, polymeric materials, fabrics, etc.

Methods

In some aspects, methods of correcting a torso deformity of a patient are provided. The subject methods generally involve positioning a torso deformity correcting device, such as a device described herein, around a torso deformity on a torso of a patient. The subject methods further include withdrawing air from the suction chamber to apply negative pressure within the suction chamber to displace the torso deformity; and setting a negative pressure level by measuring the relative distance of the torso deformity and the distal surface of the suction chamber that is indicated by the measurement component.

In certain embodiments, the elongated member is inserted fully into the port to extend all the way through the suction chamber to contact the surface of the torso deformity before suction begins. The operator of the device may begin withdrawing air from the suction chamber with a suction pump to apply negative pressure within the suction chamber. The operator may use the elongated member as an indicator of the relative distance between the distal surface of the suction chamber and the torso deformity. In some instances, the operator may use the relative distance between the distal surface of the suction chamber and the torso deformity as a guide or approximation of the distance that the torso deformity has been displaced by the suction chamber. For example, as the torso deformity is pulled outward from the torso by the suction created by the withdrawal of air from the suction chamber by the suction pump, the torso deformity pushes the elongated member out of the port. In certain embodiments, the suction chamber and/or a compressible element on the rim of the suction chamber may be compressed or otherwise displaced by the suction pressure before or during any displacement of the torso deformity.

The appropriate distance of displacement of the torso deformity for effective treatment may vary on a case by case basis and may be dependent on factors such as the severity and size of the torso deformity, age of the patient, sensitivity or pain tolerance of the patient, etc. In certain embodiments, the elongated member is not displaced by suction levels that are sufficient to move the skin of the patient but insufficient to move the torso deformity itself (e.g., the bone, cartilage, or other structure of the torso deformity, such as the sternum). In this way, the operator of the device can determine the displacement of the torso deformity without uncertainty as to whether the skin alone is being displaced.

In certain embodiments, after the negative pressure level is set by the operator of the device, the operator may view a pressure gauge that provides a visual verification of the negative pressure level inside the suction chamber. For example, a pressure gauge may be coupled to the suction chamber to provide a reading of the pressure level. In certain embodiments, the pressure gauge includes an opening and an elastic material disposed around the opening. As negative pressure is applied to the suction chamber, the elastic material is pulled within the opening to provide a visual indication of the level of negative pressure.

In certain embodiments, the elongated member may be removable from the device. For example, after the negative pressure level is set by the operator, the operator may remove the elongated member from the device. Because of the airtight port, such as described herein, no loss of air occurs and the suction pressure remains. The elongated member may be removed for any variety of reasons, e.g., such as safety purposes. The operator of the device may also use the pressure gauge that measures the negative pressure level to verify the pressure level and any changes in pressure level that may occur. The elongated member may be reinserted if additional air needs to be withdrawn, or if the suction chamber loses suction and needs to be re-applied.

In certain embodiments, the device includes a retaining element used to position the suction chamber on the torso deformity. For example, the retaining element may be a strap that may be wrapped around the patient and adjusted in length to maintain the suction chamber in position before air is withdrawn from the suction chamber.

Figure 2:
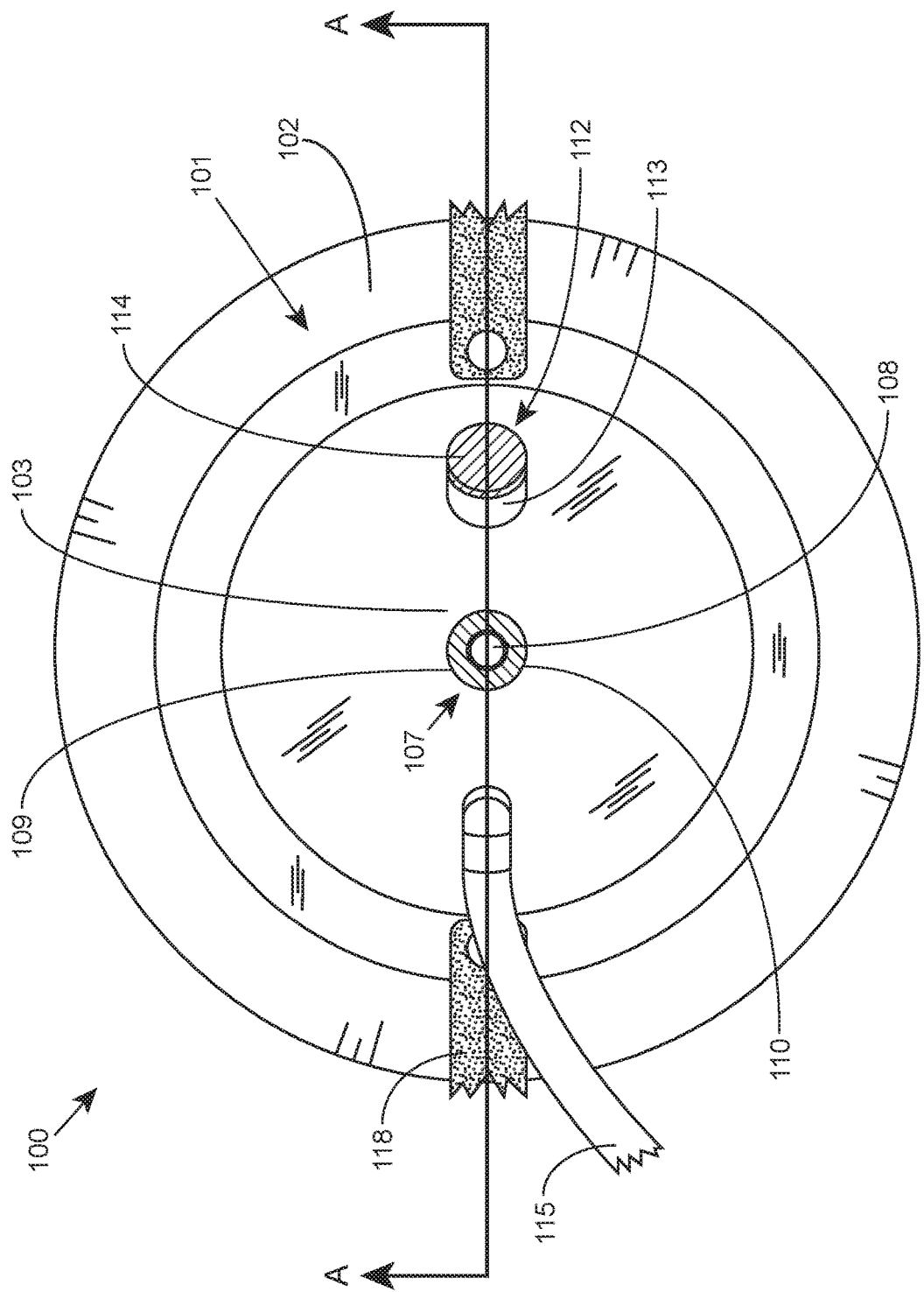
FIG. 2 illustrates a top view of the torso deformity correction device shown in FIG. 1.
Figure 3:
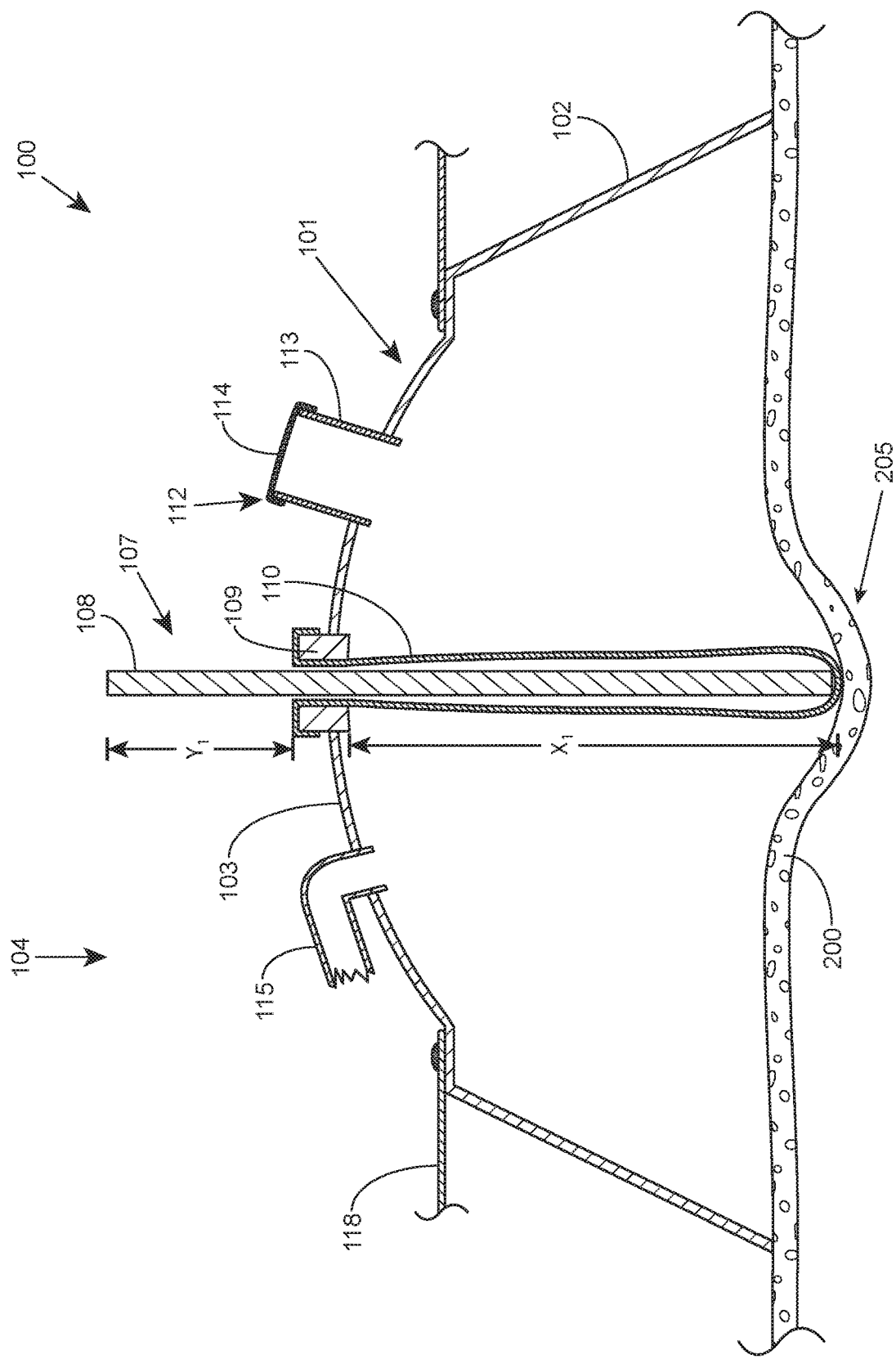
FIG. 3 illustrates a cross-sectional view of the torso deformity correction device of FIGS. 1-2 on a torso before suction is applied to the device, according to certain embodiments.
Figure 4:
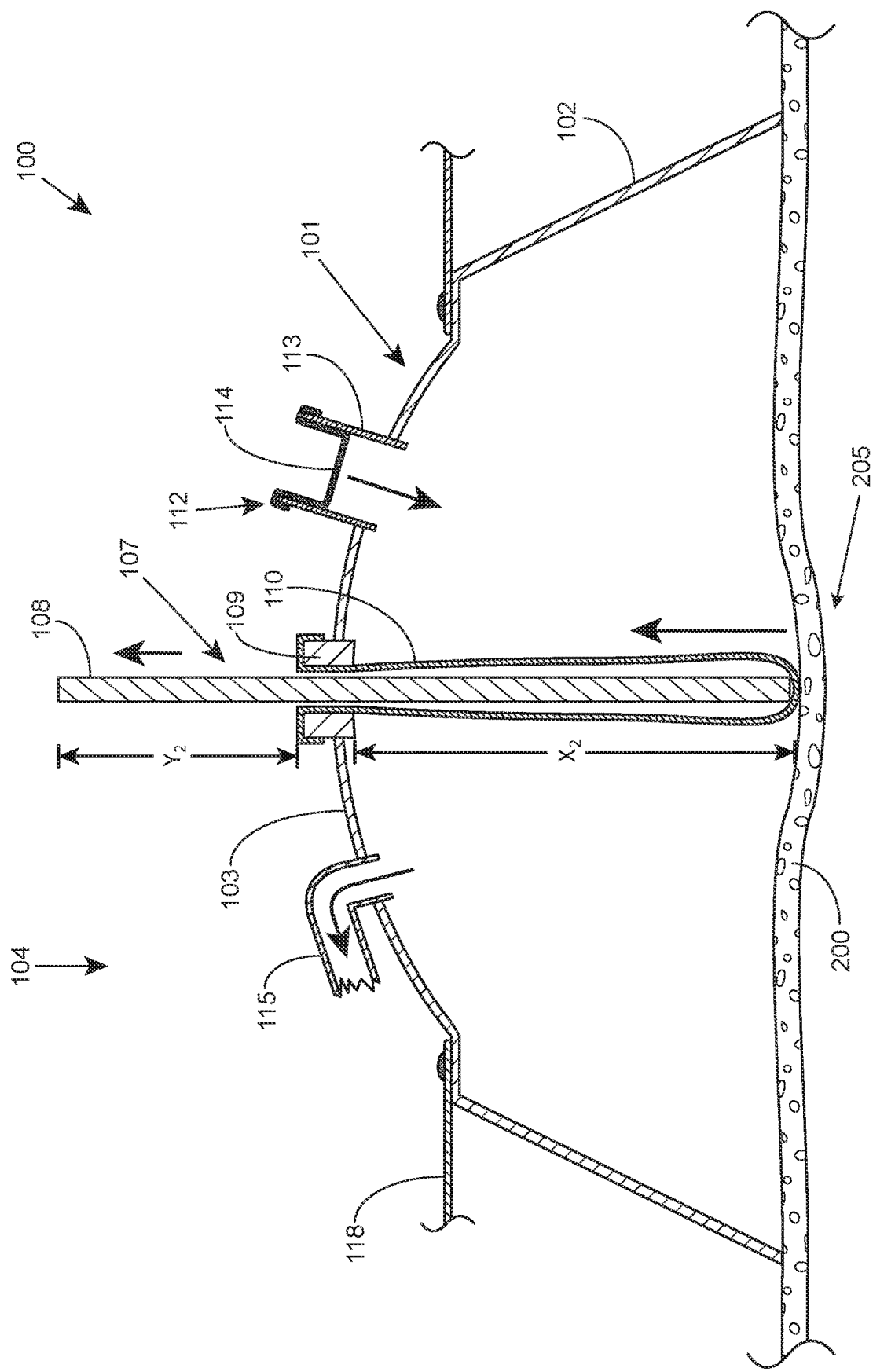
FIG. 4 illustrates a cross-sectional view of the torso deformity correction device of FIGS. 1-2 on a torso after suction is applied to the device, according to certain embodiment.

FIGS. 1-4 illustrate a torso deformity correction device, according to certain embodiments. As FIGS. 1-4 illustrate the same device, the following description is provided for all figures. FIG. 1 illustrates a perspective view of the torso deformity correction device and FIG. 2 illustrates a top view of the torso deformity correction device. FIGS. 3 and 4 illustrate a cross-sectional view of the torso deformity correction device on a torso before and after suction is applied to the device.

The correction device 100 includes a suction chamber 101. Suction chamber 101 includes a sidewall 102 and a distal surface 103 on a distal side 104. The proximal side 105 of the suction chamber 101 is open and includes the rim 106 of the sidewall 102 that contacts a torso 200 of the patient around the torso deformity 205. When the device 100 is positioned on the torso 200 of the patient, the sidewall 102, distal surface 103, and the torso 200 of the patient forms an inner space of air. When negative pressure is applied to the suction chamber to lower the pressure within the suction chamber 101, the rim 106 (which in some embodiments may comprise one or more chambers that can be filled with, e.g., air, water, gel, or other media) of the sidewall 102 presses against the torso 200 and forms an airtight seal with the torso. The negative pressure may be applied, for example, by suction pump 115 that withdraws air form the inner space in the suction chamber 101 to form a lower pressure within the suction chamber 101 than the surrounding pressure outside the suction chamber 101.

The correction device 100 also includes a measurement component 107. The measurement component 107 provides an indication of the relative distance between the torso deformity 205 and the distal surface 103 of the suction chamber, which changes as negative pressure is applied to the suction chamber 101. The measurement component 107 includes an elongated member 108 that is disposed within an airtight port 109 having a septum 110. The airtight port 109 shown includes an elongated septum 110 that extends into the suction chamber 101. The airtight septum 110 may be made from any variety of materials but should enable an airtight seal. The elongated member 108 is disposed within the airtight port 109 and the inner lumen formed by the elongated septum 110. The elongated member 108 may move within port 109 without loss of air because it remains on the outside of the elongated septum 110, which prevents loss of air from inside the suction chamber 101. The elongated septum may be made from any variety of materials but should enable and not prevent movement of the elongated member within port 109.

In the embodiment shown, the measurement component 107 is disposed in the center of the suction chamber 101. In this way, the elongated member 108 extends to the approximate center of the torso deformity that the suction chamber 101 is positioned around. It should be appreciated that in other embodiments, the elongated member 108 may not be centrally disposed in the suction chamber 101.

The elongated member 108 should be long enough to reach the surface of the torso deformity 205 while still extending beyond the port 109. When the elongated member 108 extends to the surface of the torso deformity 205, as the torso deformity 205 is displaced by the negative pressure, the torso deformity 205 pushes the elongated member 108 and displaces the elongated member 108 out the port 109. In this way, the elongated member 108 indicates the relative distance between the distal surface 103 of the suction chamber and the torso deformity 205. The elongated member 108 is shown including indicator markings that facilitate determining the relative distance between the torso deformity 205 and the distal surface 103 of the suction chamber. It should be appreciated the distal surface 103 is a relative reference point that is used to represent the distance to the torso deformity 205. The precise location on the distal surface 103 may vary. For example, if the port 109 is centrally located within the distal surface, then the elongated member may provide a relative distance between the port 109 at the distal surface 103 and the torso deformity 205.

It should be appreciated that the suction chamber 101 may compress or otherwise shift closer to the torso 200 upon application of negative pressure within the suction chamber 101. Furthermore, in another embodiment, the rim 106 of the suction chamber 101 may include a compressible element that compresses when negative pressure is applied. For example, the rim 106 may include rubber, other soft polymeric materials, or an air-filled chamber, that compresses when negative pressure is applied to the suction chamber. Therefore, it should be appreciated that the compression of the suction chamber and/or the compressible element on the rim may cause a change in the relative distance between the torso deformity 205 and the distal surface 103 of the suction chamber.

The depicted correction device 100 also optionally includes pressure gauge 112 that provides a visual verification of the negative pressure level inside the suction chamber. The pressure gauge 112 indicates negative pressure level rather than distance of the relative distance between the torso deformity and the suction chamber. The pressure gauge 112 shown includes a protruding cylindrical sidewall 113 with an opening at the end distal to the suction chamber 101. An elastic material 114 is disposed around the distal opening of the sidewall 113. As the negative pressure is applied to the suction chamber, the elastic material 114 is pulled within the opening to provide a visual indication of the level of negative pressure. Indicator markings are provided on the sidewall 113 to represent the negative pressure level associated with the amount of displacement of the elastic material 114.

The correction device 100 also includes suction pump 115 that is operably coupled to the suction chamber 101. The suction pump 115 is coupled to a port at the distal surface of the suction chamber 101. The suction pump 115 includes a bulb 116, which may be manually pumped by an operator of the device to withdraw air from the suction chamber 101. It should be appreciated that in other embodiments, other types of pumps other than a bulb may be implemented, such as an electric vacuum source. The depicted suction pump 115 also includes a shutoff valve 117. In certain embodiments, the shutoff valve may also be coupled to an additional, optional pressure gauge 119 that can be used to measure the negative pressure inside the suction chamber.

The correction device 100 also includes retaining element 118 that maintains the suction chamber in place when positioned around the torso deformity 205. This may assist the placement of the suction chamber 101 around the torso deformity by holding it in place before sufficient negative pressure is applied to form a suction to the torso. The retaining element 118 may be made from any variety of materials and is coupled to the sides of the suction chamber. The retaining element 118 is positioned around the patient and may be adjusted in length to maintain the suction chamber in place before using the suction pump 115.

In use, the torso deformity correcting device 100 is positioned such that the proximal side of the suction chamber 101 is positioned on a torso 200 of a patient. The rim 106 is positioned around the torso deformity 205 and the retaining element 118 is then wrapped around the patient and adjusted in length to maintain the suction chamber 101 in position. The elongated member 108 may be fully inserted into port 109 and within the lumen formed by the elongated septum 110—e.g., by the operator, such as a physician or caregiver, for instance. In this way, the elongated member 108 is extended all the way through the suction chamber 101 and brought into contact with the surface of the torso deformity 205. FIG. 3 illustrates the torso deformity correcting device 100 at this reference time point—when the suction chamber is positioned and the retaining element is secured, but before any significant negative pressure is applied to the suction chamber 101. As shown in FIG. 3, as there is no significant negative pressure applied at this point, the elastic element 114 remains across the distal opening of the measurement component 112 without being stretched or otherwise displaced by negative pressure.

The operator of the device may begin withdrawing air from the suction chamber 101 with the suction pump to apply negative pressure within the suction chamber 101. In other words, the withdrawal of air form the suction chamber 101 creates a lower pressure within the suction chamber 101 than outside the suction chamber 101, which provides a suction effect to the torso deformity 205. The torso deformity 205 is pulled outward from the torso by the suction created by the withdrawal of air from the suction chamber 101 by the suction pump 115. As the torso deformity 205 is displaced outward, the torso deformity 205 pushes the elongated member 108 out of port 109. For example, as shown in FIG. 3, the distance between the surface of the torso deformity 205 and the distal surface 103 of the suction chamber 101 is $X_1$. Moreover, the length of the portion of the elongated member that extends out of the port 109 is a length of $Y_1$. It should be appreciated that the exact points of reference may be different without compromising the underlying principles. For example, the distance $X_1$ may refer generally to the distance between the torso deformity 205 and the port 109.

In FIG. 4, the torso deformity 205 is displaced outward by suction and the elongated member 108 is pushed out port 109. For instance, the distance $X_2$ from the torso deformity 205 to the distal surface 103 (or port 109) is now a shorter distance than the distance $X_1$ in FIG. 3. Furthermore, the length $Y_2$ of the portion of the elongated member 108 extending out of the port 109 is now longer than the distance $Y_1$ in FIG. 3.

The elongated member 108 is pushed out port 109 by a length equal to the distance that the torso deformity 205 is displaced by suction. In this way, the operator of the device 100 is able to withdraw air from the suction chamber while being able to visually monitor the distance that the torso deformity 205 is being displaced. The operator may be able to determine the appropriate distance of displacement of the torso deformity for effective treatment. The amount of displacement of the torso deformity may vary on a case by case basis and may be dependent on factors such as severity and size of the torso deformity, age of the patient, sensitivity or pain tolerance of the patient, etc.

In certain embodiments, the elongated member is not displaceable by suction of the skin alone, without displacement of the torso deformity (e.g., the bone, cartilage, or other structure of the torso deformity, such as the sternum). In this way, the operator of the device 100 is able to determine displacement of the torso deformity without uncertainty as to whether the skin alone is being displaced. In certain aspects, the measurement component 107 enables the operator to avoid having to rely on visual inspection of the torso deformity alone, through device 100 and without any indication as to whether only the skin is being displace by suction or whether the torso deformity (e.g., the bone, cartilage, or other structure of the torso deformity, such as the sternum) is also being displaced. Moving the skin alone, without displacement of the torso deformity (e.g., the bone, cartilage, or other structure of the torso deformity, such as the sternum), may lead to not enough suction pressure being applied and resulting in less effective treatment. In addition, moving the skin alone may cause negative effects for the patient, such as skin avulsion or hematoma formation.

As shown in FIG. 4, the suction pump 115 is used by the operator to withdraw air from the suction chamber (as represented by the arrow direction in suction pump 115). As air is withdrawn, the negative pressure is increased, and the resulting force from the suction is increased. As a result, the elastic material 114 on measurement component 112 is displaced proportionally by the generated suction. Furthermore, the generated suction pulls the torso deformity 205 outward, which displaces the elongated member 108 out of the port 109. The operator may visually monitor the indicator markings 111 on the portion of the elongated member 108 that is outside the port 109 to determine the distance that the torso deformity has been displaced. The operator may then set the appropriate suction pressure accordingly since the elongated member 108 is pushed out port 109 by a length equal to the distance that the torso deformity 205 is displaced by suction.

Again, it should be appreciated that the compression of the suction chamber and/or the compressible element on the rim may cause a change in the relative distance between the torso deformity 205 and the distal surface 103 of the suction chamber 101. In such case, the operator may view the indicator markings 111 to determine the change in relative distance between the distal surface 103 and torso deformity 205, which may provide an indication of the amount of pressure and/or an approximation of the amount of displacement that has occurred.

In certain embodiments, the operator may remove the elongated member from the device after the negative pressure level is set by the operator. In such case, the elongated member is removably coupled to the suction chamber 101. Because of the airtight port, such as described herein, no loss of air occurs and the suction pressure remains. The elongated member may be removed for any variety of reasons, e.g., such as safety purposes. The operator of the device may now use the pressure gauge that measures the negative pressure level to verify the pressure level and any changes in pressure level that may occur during use of the device. The elongated member may be reinserted if additional air needs to be withdrawn.

In certain embodiments, the operator uses a retaining element on the device to position the device on the torso of the patient before suction is applied. For example, the retaining element may be a strap that may be wrapped around the patient and adjusted in length to maintain the suction chamber in position before air is withdrawn from the suction chamber.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A device for correcting a torso deformity of a patient, the device comprising:
   a suction chamber for placement around the torso deformity and to provide negative pressure to the torso deformity; and
   a measurement component coupled to the suction chamber;
   wherein the measurement component comprises an elongated member moveably coupled to the suction chamber through an air-tight port comprising a septum extending into the suction chamber, and configured to be displaceable by movement of the torso deformity in response to the negative pressure and to visually indicate a relative distance between a distal surface of the suction chamber and the torso deformity, the elongated member comprising a first end positioned external to the suction chamber and a second end positioned internal to the suction chamber.

2. The device of claim 1, wherein the septum is an elongated septum defining an inner lumen, and wherein the elongated member is disposed within the air-tight port and the elongated septum, such that the second end of the elongated member is positioned completely within the inner lumen defined by the elongated septum.

3. The device of claim 1, wherein the air-tight port is located in a central portion of the suction chamber.

4. The device of claim 1, wherein the elongated member comprises a plurality of indicator marks.

5. The device of claim 1, wherein the elongated member is removable.

6. The device of claim 1, further comprising a pressure gauge that provides a visual verification of the negative pressure level inside the suction chamber.

7. The device of claim 6, wherein the pressure gauge comprises an elastic material that is displaced as a function of the amount of negative pressure applied to the suction chamber.

8. The device of claim 1, further comprising a retaining element coupled to the suction chamber to maintain the suction chamber in place when positioned around the torso deformity.

9. The device of claim 1, further comprising a suction pump operably coupled to the suction chamber for withdrawal of air contained between the suction chamber and the torso when the suction chamber is positioned around the torso deformity.

10. A method of correcting a torso deformity of a patient, the method comprising:
- positioning a torso deformity correcting device around the torso deformity on a torso of the patient, wherein the device comprises:
- a suction chamber for placement around the torso deformity and to provide negative pressure to the torso deformity; and
- a measurement component coupled to the suction chamber;
- wherein the measurement component comprises an elongated member moveably coupled to the suction chamber through an air-tight port comprising a septum extending into the suction chamber and configured to be displaceable by movement of the torso deformity in response to the negative pressure and to visually indicate a relative distance between a distal surface of the suction chamber and the torso deformity, the elongated member comprising a first end positioned external to the suction chamber and a second end positioned internal to the suction chamber, wherein the device is positioned such that the second end is in contact with the torso deformity;
- withdrawing air from the suction chamber to apply negative pressure within the suction chamber to displace the torso deformity; and
- setting a negative pressure level based upon the relative distance of the torso deformity and the distal surface of the suction chamber that is indicated by the measurement component.

11. The method of claim 10, wherein the septum is an elongated septum defining an inner lumen, and wherein the elongated member is disposed within the air-tight port and the elongated septum, such that the second end of the elongated member is positioned completely within the inner lumen defined by the elongated septum.

12. The method of claim 10, wherein the air-tight port is located in a central portion of the suction chamber.

13. The method of claim 10, wherein the elongated member comprises a plurality of indicator marks.

14. The method of claim 10, wherein the elongated member is removably coupled to the suction chamber, and wherein the method further comprises removing the elongated member from the suction chamber after the negative pressure level is set.

15. The method of claim 10, wherein the device further comprises a pressure gauge that provides a visual verification of the negative pressure level inside the suction chamber, and wherein the method further comprises visually verifying the negative pressure level set inside the suction chamber with the pressure gauge.

16. The method of claim 15, wherein the method further comprises removing the elongated member from the suction chamber after the negative pressure level is set, and wherein the negative pressure level is visually verified after the elongated member is removed.

17. The method of claim 15, wherein the pressure gauge comprises an elastic material that is displaced as a function of the amount of negative pressure applied to the suction chamber.

18. The method of claim 10, wherein the device further comprises a retaining element coupled to the suction chamber, and wherein the method further comprises retaining the suction chamber around the torso deformity with the retaining element after the suction chamber is positioned around the torso deformity.

19. The device of claim 10, wherein the device further comprises a suction pump operably coupled to the suction chamber, and wherein the method further comprises withdrawing air contained between the suction chamber and the torso with the suction pump when the suction chamber is positioned around the torso deformity.

\* \* \* \* \*